US006171578B1

(12) United States Patent
Dean et al.

(10) Patent No.: US 6,171,578 B1
(45) Date of Patent: Jan. 9, 2001

(54) BENZODIAZEPINE DERIVATIVES FOR IMAGING THROMBI

(75) Inventors: Richard T. Dean; John Lister-James, both of Bedford, NH (US); Michael C. Venuti, San Francisco; Todd C. Somers, San Carlos, both of CA (US)

(73) Assignees: Diatide, Inc., Londonderry, NH (US); Genentech, Inc., San Francisco, CA (US)

(*) Notice: Under 35 U.S.C. 154(b), the term of this patent shall be extended for 0 days.

(21) Appl. No.: 09/292,067

(22) Filed: Apr. 14, 1999

(51) Int. Cl.[7] ............................ A61K 51/00; A61M 36/14
(52) U.S. Cl. .................. 424/1.69; 424/1.11; 424/1.65; 424/9.1; 540/504; 540/569; 540/518; 544/285; 534/14; 514/213
(58) Field of Search .................. 424/1.65, 1.69, 424/9.1, 9.3, 9.4, 9.5, 9.6, 9.7, 1.11; 534/7, 10–16; 530/300, 324–330, 322, 395; 540/504, 569, 518; 544/285

(56) References Cited

U.S. PATENT DOCUMENTS

| 4,656,026 | 4/1987 | Coffman et al. . |
| 4,777,169 | 10/1988 | Earley et al. . |
| 4,885,152 | 12/1989 | Nakatsuka et al. . |
| 4,997,771 | 3/1991 | Barnett et al. . |
| 5,096,695 | 3/1992 | Carmann et al. . |
| 5,645,815 | 7/1997 | Dean et al. . |
| 5,663,166 | 9/1997 | Blackburn et al. . |
| 5,830,856 | 11/1998 | Dean et al. . |

FOREIGN PATENT DOCUMENTS

| 5-310711 | 11/1993 | (JP) . |
| WO 95/12610 | 5/1995 | (WO) . |

OTHER PUBLICATIONS

Blackburn, et al., (1997) "From Peptide to Non–Peptide. 3. Atropisomeric GPIIbIIIa Antogonists Containing the 3,4 Dihydro–1H–1,4–benzodiazepine–2,5–dione Nucleus" J. Med. Chem. 40, 717–759.

Ku, et al. (1993) "Direct Design of a Potent Non–Ppetide Fibrinogen Receptor Antagoist Based on the Structure and Conformation of a Highly constrained Cycle RGD Peptide" J. Am. Chem. Soc. 115, 8861–8862.

McDowell, et al., (1994) "From Peptide to Non–Peptide. 1. The Elucidation of Bioactive Conformation of the Arginine–Glycine–Aspartic Acid Recongnition Sequence" J. Am. Chem Soc. 116, 5069–5076.

McDowell, et al, (1994) "From Peptide to Non–Peptide. 2. The de Novo Design of Potene, Non–Peptidal Inhibitors of Platelet Aggregation Based on Benzodiazepinedione Scaffold" J. Am. Chem. Soc. 116, 5077–5083.

Zucker, et al. (1989) "Platelet Aggregation Measured by the Photometric Method" Methods in Enzymology 169, 117–133.

Primary Examiner—Diana Dudash
Assistant Examiner—Dameron Jones
(74) Attorney, Agent, or Firm—Patricia A. McDaniels

(57) ABSTRACT

The invention provides compounds comprising glycoprotein IIb/IIIa receptor-binding benzodiazepine derivatives covalently linked to metal ion chelators. The compounds of the invention may be labeled with a radionuclide such as $^{99m}$Tc and used to image thrombi.

25 Claims, No Drawings

BENZODIAZEPINE DERIVATIVES FOR IMAGING THROMBI

The present invention relates to the field of diagnostic imaging of thrombosis. More particularly, the invention relates to pharmaceutical compositions for imaging thrombi.

BACKGROUND OF THE INVENTION

Thrombi are blood clots which form within the cardiovascular system. Formation of thrombi, i.e., thrombosis, may cause local obstruction of blood vessels, for example in veins, arteries, or capillaries. Venous thrombi usually form in lower limbs and may produce acute symptoms by causing inflammation of the vessel wall or obstruction of the vein. Pieces of venous thrombi may also circulate through the cardiovascular system to form a plug, or embolus, at a distant site such as the lung. Arterial thrombi are commonly associated with vascular disease such as atherosclerosis and may produce tissue ischemia (local anemia) by obstructing blood flow or by embolizing into capillaries. Thrombi may also form in the heart, for example, on inflamed or damaged valves, on tissue adjacent to myocardial infarcts, within injured chambers, or on prosthetic valves.

While all thrombi contain the protein fibrin and blood cells, the proportions of particular blood cells present and of fibrin/blood cell may differ, for example, because of the blood flow at the site of thrombus formation and thrombus age. Arterial thrombi which form at sites of high blood flow contain platelet aggregates bound together by thin fibrin strands. Venous thrombi form in areas of stagnant blood flow and contain red blood cells with interspersed fibrin and fewer platelets. Thrombi which form under conditions of slow to moderate flow contain a mixture of red cells, platelets, and fibrin. Leukocytes, the white blood cells, migrate to and become incorporated into thrombi as they age. In addition, aggregated platelets in aging thrombi lyse and are replaced by fibrin.

Accurate detection of the various kinds of thrombi is necessary to choose, to optimize and to monitor treatment, which may differ by virtue of the location and nature of the thrombus. Recently, ACUTECT™, a kit for making the $^{99m}$Tc-radiolabeled peptide, apcitide, was approved for sale in the U.S. as a radiopharmaceutical product for imaging acute deep vein thrombosis (DVT). The commercial availability of ACUTECT™ will significantly improve the accuracy of detection of acute DVT, and consequently, treatment of such thrombi. However, no radiopharmaceutical has thus far been approved for detection of other kinds of thrombi, and the most accurate methods available for detection of other venous thrombi such as pulmonary emboli and of arterial thrombi are invasive. Additional non-invasive agents capable of detecting the various kinds of thrombi are needed. $^{99m}$Tc-radiolabeled apcitide binds to the GPIIb/IIIa receptor, the most abundant glycoprotein on the surface of platelets. The GPIIb/IIIa receptor is required for platelet aggregation and is a critical component of thrombus formation, functioning as the receptor for the adhesive proteins fibrinogen (the precursor of fibrin), fibronectin, von Willebrand factor, and vitronectin. The interaction between GPIIb/IIIa and its natural ligands is mediated by the tripeptide sequence arginine-glycine-aspartic acid (RGD). Apcitide contains the tripeptide—L-[S-(3-aminopropyl)cysteine]-glycine-aspartic acid—, which is believed to interact with GPIIb/IIIa.

U.S. Pat. No. 5,645,815 discloses that high quality thrombus imaging agents comprise GPIIb/IIIa receptor binding compounds which are capable of inhibiting platelet aggregation with an $IC_{50}$ less than about 0.3 $\mu$M. U.S. Pat. No. 5,830,856 discloses that such imaging agents may comprise GPIIb/IIIa receptor binding compounds which are capable of inhibiting platelet aggregation with an $IC_{50}$ less than about 1.0 $\mu$M.

One class of GPIIb/IIIa binding platelet aggregation inhibitors, disclosed in U.S. Pat. Nos. 5,403,836; 5,493,020; 5,565,449; 5,663,166; 5,674,863; 5,674,865; 5,705,890; and 5,716,951, are substituted benzodiazepinediones. The benzodiazepinedione scaffold approximates the "cupped" configuration of the RGD tripeptide, which correlates with platelet aggregation inhibitory activity. U.S. Pat. Nos. 5,403,836; 5,493,020; 5,565,449; 5,663,166; 5,674,863; 5,674,865; 5,705,890; and 5,716,951 describe several large classes of benzodiazepinedione derivatives, including derivatives of the general formula:

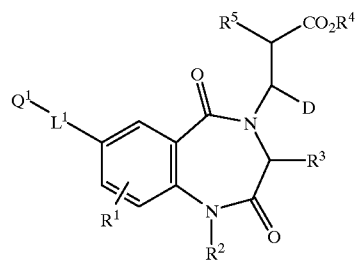

where $R^1$, $R^2$, and $R^4$ are each independently H or a reactive group; $R^3$ and $R^5$ are each independently H, alkyl, substituted alkyl, aryl, substituted aryl, or a combination thereof; D is hydrogen, phenyl, or lower alkyl; $L^1$ is a linking moiety; and $Q^1$, is a positively charged nitrogen-containing moiety. The substituted benzodiazepinediones of U.S. Pat. Nos. 5,403,836; 5,493,020; 5,565,449; 5,663,166; 5,674,863; 5,674,865; 5,705,890; and 5,716,951 are exclusively described as therapeutic agents.

Ku, et al. (1993) *J. Amn. Chem. Soc.* 115, 8861–8862 describes design and synthesis of benzodiazepine derivatives useful as inhibitors of glycoprotein IIb/IIIa receptor mediated platelet aggregation. The 1,4-benzodiazepine derivatives of Ku, et al. are exclusively described as potential antithrombotic agents.

U.S. Pat. No. 4,656,026 describes spin-labeled benzodiazepines for magnetic resonance imaging of brain tissue. U.S. Pat. No. 4,777,169 discloses radioiodinated benzodiazepines used in radioimmunoassays to determine benzodiazepine levels in body fluids. U.S. Pat. No. 4,885,152 describes radioiodinated and radiobrominated benzodiazepine derivatives for detection of benzodiazepine receptors in cerebral diseases. U.S. Pat. No. 4,997,771 discloses $^3$H-benzodiazepines used to assay benzodiazepine receptor binding activity. U.S. Pat. No. 5,096,695 discloses radioiodinated benzodiazepine derivatives for use as brain imaging agents. WO 95/12610 discloses N-alkyl peptide chelators which may be covalently linked to a variety of ligands, including benzodiazepines, for use in complexing rhenium or technetium ions. JP 5-310711 discloses N-substituted benzodiazepin-2-one derivatives for electron spin resonance imaging of benzodiazepine receptors in brain nerves to diagnose epilepsy, parkinsonism, cerebral ischemia and cerebral edema.

SUMMARY OF THE INVENTION

The present inventors have found that benzodiazepine derivatives may be employed as effective thrombus imaging agents.

In one embodiment, the invention provides a compound comprising a glycoprotein IIb/IIIa receptor binding benzodiazepine derivative covalently linked to a metal ion chelator, wherein the compound retains substantial potency, as measured in a standard assay for inhibition of platelet aggregation.

In another embodiment, the invention provides a compound having a formula:

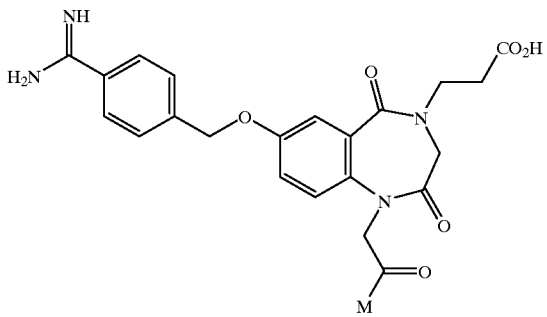

wherein M is a metal ion chelator.

In another embodiment, the invention provides a scintigraphic imaging agent comprising a γ-emitting radionuclide and a compound of the invention.

In another embodiment, the invention provides a complex of a γ-emitting radionuclide and a compound of the invention.

In yet another embodiment, the invention provides a $^{99m}Tc$ chelate of a compound comprising a glycoprotein IIb/IIIa receptor binding benzodiazepine covalently linked to a metal ion chelating moiety, wherein the compound retains substantial potency for inhibition of human platelet aggregation, as measured in a standard inhibition of platelet aggregation assay, when chelated to $^{99m}Tc$, and wherein the chelate contains at least one sulfur ligand bound to $^{99m}Tc$.

In another embodiment, the invention provides a method of detecting a thrombus in a mammalian body, comprising the steps of administering an effective diagnostic amount of the scintigraphic imaging agent or complex of the invention to the body and detecting radiation localized at the thrombus.

DETAILED DESCRIPTION OF THE INVENTION

The patent and scientific literature referenced herein establish the knowledge available to those with skill in the art. The issued U.S. patents and allowed applications are hereby incorporated by reference.

The compounds of the invention comprise a glycoprotein IIb/IIIa receptor-binding benzodiazepine moiety and a metal ion chelating moiety. In accordance with the invention, the terms "benzodiazepine derivative" or "benzodiazepine moiety" are interchangeable and are defined as including any molecule comprising the benzodiazepine nucleus, i.e., a seven-membered ring fused to an aromatic six-membered ring. The compounds of the invention may comprise any benzodiazepine moiety, so long as the compound retains substantial potency, as measured by the inhibitory concentration at 50% ($IC_{50}$) of the compound for human platelet aggregation in a standardized assay of inhibition of platelet aggregation, such as the assay set forth in Zucker, *Methods in Enzymology* (1989) 169, 117–133. As defined herein, "substantial potency" is defined as: preferably, an $IC_{50}$ for inhibition of human platelet aggregation of less than about 1 μM; more preferably, an $IC_{50}$ for inhibition of human platelet aggregation of less than about 0.3 μM; and most preferably, an $IC_{50}$ for inhibition of human platelet aggregation of less than about 0.1 μM.

Preferably, the substituted 1,4-benzodiazepine derivatives disclosed in Ku et al., supra, are used as the benzodiazepine moiety of the compounds of the invention, so long as the substituted benzodiazepine can be further derivatized for covalent attachment of a metal ion chelator without substantially affecting the platelet aggregation inhibitory activity of the benzodiazepine. Similarly, any of the substituted benzodiazepinediones disclosed in U.S. Pat. Nos. 5,403,836; 5,493,020; 5,565,449; 5,663,166; 5,674,863; 5,674,865; 5,705,890; and 5,716,951 is employed as the benzodiazepine moiety of the compounds of the present invention, so long as the substituted benzodiazepinedione can be further derivatized for covalent attachment of a metal ion chelator without substantially affecting the platelet aggregation inhibitory activity of the benzodiazepinedione. More preferably, the substituted 1,4-benzodiazepine-2,5-diones disclosed and claimed in U.S. Pat. No. 5,663,166, are used as glycoprotein IIb/IIIa binding moieties in the compounds of the invention. Most preferably, substituted 1,4-benzodiazepine-2,5-diones corresponding to the formulae set forth below are used as glycoprotein IIb/IIIa binding moieties in the compounds of the invention.

In one embodiment, the invention provides a compound having a formula:

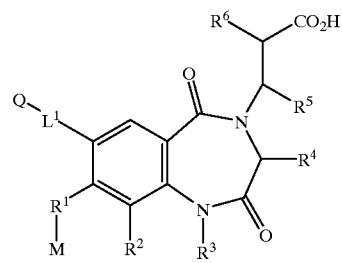

where $R^1$ is $C_1$–$C_8$ lower alkyl, $R^2$, $R^3$, $R^4$, $R^5$, and $R^6$ are each independently H, $C_1$–$C_8$ lower alkyl, substituted $C_1$–$C_8$ alkyl, aryl, substituted aryl, or a combination thereof; $L^1$ is a linking moiety; Q is a positively charged nitrogen-containing moiety; and M is a metal ion chelator.

As defined herein, "substituted $C_1$–$C_8$ alkyl" means an alkyl of the designated length substituted with a hydroxyl group, an ether, a thioether, a $C_1$–$C_8$ branched hydrocarbon, a $C_1$–$C_8$ straight chain hydrocarbon, an amine, a primary alkylamine, a secondary alkylamine, a primary arylamine, a secondary arylamine, a primary alkylsilicate, a secondary alklysilicate, a tertiary alkylsilicate, and the like. In accordance with the invention, "aryl" may be saturated or unsaturated and may optionally be a heterocycle. A "substituted aryl" of the invention means an aryl which may optionally be a heterocycle and which is substituted at one or more positions with a hydroxyl group, an ether, a thioether, a $C_1$–$C_8$ branched hydrocarbon, a $C_1$–$C_8$ straight chain hydrocarbon, an amine, a primary alkylamine, a secondary alkylamine, a primary arylamine, a secondary arylamine, a nitro group, a halogen, a sulfonic acid, an alkylsulfonyl, a sulfonamide, and the like.

In another embodiment, the invention provides a compound having a formula:

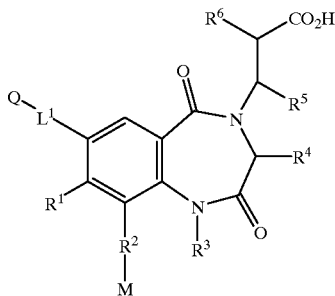

where $R^2$ is $C_1$–$C_8$ lower alkyl, $R^1$, $R^3$, $R^4$, $R^5$, and $R^6$ are each independently H, $C_1$–$C_8$ lower alkyl, substituted $C_1$–$C_8$ alkyl, aryl, substituted aryl, or a combination thereof; $L^1$ is a linking moiety; Q is a positively charged nitrogen-containing moiety; and M is a metal ion chelator.

In another embodiment, the invention provides a compound having a formula:

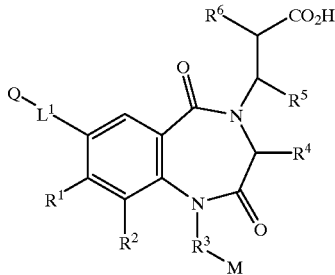

where $R^3$ is $C_1$–$C_8$ lower alkyl; $R^1$, $R^2$, $R^4$, $R^5$, and $R^6$ are each independently H, $C_1$–$C_8$ lower alkyl, substituted $C_1$–$C_8$ alkyl, aryl, substituted aryl, or a combination thereof; $L^1$ is a linking moiety; Q is a positively charged nitrogen-containing moiety; and M is a metal ion chelator.

In another embodiment, the invention provides a compound having a formula:

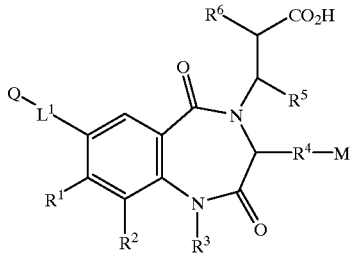

where $R^4$ is $C_1$–$C_8$ lower alkyl; $R^1$, $R^2$, $R^3$, $R^5$, and $R^6$ are each independently H, $C_1$–$C_8$ lower alkyl, substituted $C_1$–$C_8$ alkyl, aryl, substituted aryl, or a combination thereof; $L^1$ is a linking moiety; Q is a positively charged nitrogen-containing moiety; and M is a metal ion chelator.

In another embodiment, the invention provides a compound having a formula:

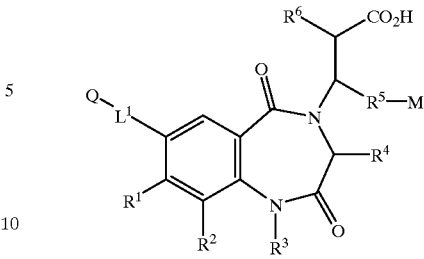

where $R^5$ is $C_1$–$C_8$ lower alkyl; $R^1$, $R^2$, $R^3$, $R^4$, and $R^6$ are each independently H, $C_1$–$C_8$ lower alkyl, substituted $C_1$–$C_8$ alkyl, aryl, substituted aryl, or a combination thereof; $L^1$ is a linking moiety; Q is a positively charged nitrogen-containing moiety; and M is a metal ion chelator.

In another embodiment, the invention provides a compound having a formula:

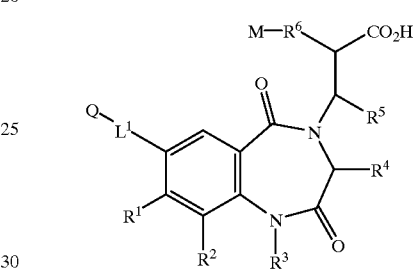

where $R^6$ is $C_1$–$C_8$ lower alkyl; $R^1$, $R^2$, $R^3$, $R^4$, and $R^5$ are each independently H, $C_1$–$C_8$ lower alkyl, substituted $C_1$–$C_8$ alkyl, aryl, substituted aryl, or a combination thereof; $L^1$ is a linking moiety; Q is a positively charged nitrogen-containing moiety; and M is a metal ion chelator.

In each of the formulae set forth above, linking moiety $L^1$ is a bivalent radical containing from about 3 to about 9 methylene groups, or $L^1$ may be a bivalent radical having a length equivalent to from about 3 to about 9 methylene groups. Preferably, $L^1$ has a length equivalent to from about 4 to about 6 methylene groups. More preferably, $L^1$ has a length equivalent to about 5 methylene groups. $L^1$ preferably contains one or more $sp^2$ or sp atoms and thus is constrained. In accordance with the invention, $L^1$ may contain one or more alkene, alkyne, aryl, heterocycle groups, or a functional group or groups containing N, O, or S. Preferably, $L^1$ comprises a ketone, sulfoxide, secondary amine, amide, ureido, carbamate, sulfonamide, or sulfone. More preferably, $L^1$ comprises a thioether. Most preferably, $L^1$ comprises an ether, in particular, an alkylether such as a methylether.

Positively charged moiety Q contains one or more nitrogen atoms and has a $pK_b$ sufficiently high that said atoms are at least 10% positively charged at physiological pH. In accordance with the invention, Q may comprise one or more primary, secondary, tertiary, or quaternary amines or imines either isolated or conjugated with other nitrogen atoms. Alternatively, Q may be a saturated or unsaturated (including aromatic) heterocyclic group, provided that said group bears a positive charge at physiological pH. In accordance with the invention Q may be selected from but is not limited to such groups as: amino, imino, amidino, aminomethyleneimino, aminomethyleneamino, iminomethylamino, guanidino, $N^G$-aminoguanidino, alkylamino, dialkylamino, trialkylamino, alkylideneamino, pyranyl, pyrroyl, imidazolyl, pyrazolyl, pyridyl, pyrazinyl, pyrimidinyl, pyridazinyl, indolizinyl, isoindolyl, 3H-indolyl, indolyl, 1H-indazolyl, purinyl, 4H-quinolizinyl, isoquinolyl, quinolyl, phthalazinyl, naphthyridinyl, quinoxalinyl, quinazolinyl, cinnolinyl, pteridinyl, 4aH-carbazolyl, carbazolyl, b-carbolinyl, phenanthridinyl, acridinyl, phenanthrolinyl, phenazinyl, phenarsazinyl, phenothiazinyl, pyrrolinyl, imidazolidinyl, imidazolinyl, pyrazolidinyl, pyrazolinyl, piperidyl, piperazinyl, indolinyl, isoindolinyl, quinuclidinyl, morpholinyl, 1,3-diazacyclohex-4-ene, and multiples thereof. Optionally, any of the nitrogen-containing heterocycles set forth above may be substituted with amino, imino, amidino, aminomethyleneamino, iminomethylamino, guanidino, $N^G$-amino-guanidine, alkylamino, dialkylamino, trialkylamino, or alkylidene-amino groups. Preferably, Q is a amidino or substituted amidino group.

Methods for making substituted glycoprotein IIb/IIIa receptor binding benzodiazepinediones are disclosed in U.S. Pat. Nos. 5,403,836; 5,493,020; 5,565,449; 5,663,166; 5,674,863; 5,674,865; 5,705,890; and 5,716,951 and in Example 1 below. Methods for making substituted glycoprotein IIb/IIIa receptor binding benzodiazepines are disclosed in Ku et al., supra.

The compounds of the invention may comprise any metal ion chelator. The metal ion chelator may be covalently linked to the substituted benzodiazepine at any position of the benzodiazepine scaffold, so long as the presence of the chelator does not substantially interfere with the compound's ability to bind to the glycoprotein IIb/IIIa receptor. By "substantially interfere" is meant that the compound retains some potency for inhibition of human platelet aggregation, as defined above.

For example, the compounds of the invention may comprise a metal ion chelator having a formula:

$$C(pgp)^s\text{-}(aa)\text{-}C(pgp)^s$$

where $(pgp)^s$ is hydrogen or a thiol protecting group and (aa) is any α- or β-amino acid not comprising a thiol group. In a preferred embodiment, the amino acid is glycine. Methods for making such a metal ion chelator are set forth in U.S. Pat. Nos. 5,654,272; 5,681,541; 5,788,960; and 5,811,394.

Alternatively, the compound of the invention may comprise a metal ion chelator of capable of forming an electrically neutral complex with the metal ion, as set forth in U.S. Pat. Nos. 5,720,934; 5,776,428; and 5,780,007; in allowed U.S. Ser. Nos. 08/467,791, 08/468,964; and 08/170,299; and in U.S. Ser. No. 07/871,282. Such chelators include but are not limited to:

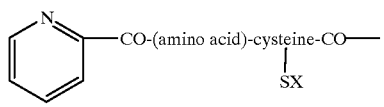

wherein X=H or a protecting group;
(amino acid)=any amino acid;

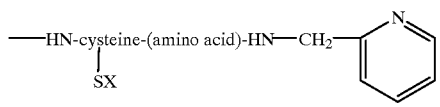

wherein X=H or a protecting group;
(amino acid)=any amino acid;

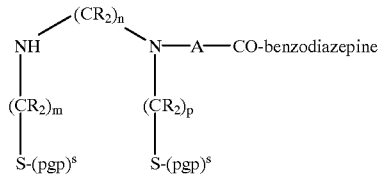

wherein each R can be independently H, $CH_3$ or $C_2H_5$; each $(pgp)^s$ can be independently a thiol protecting group or H; m, n and p are independently 2 or 3; A is linear $C_1$–$C_8$ alkyl, substituted linear $C_1$–$C_8$ alkyl, cyclic $C_3$–$C_8$ alkyl, substituted cyclic $C_3$–$C_8$ alkyl, aryl, substituted aryl, or a combination thereof; and X is benzodiazepine; and

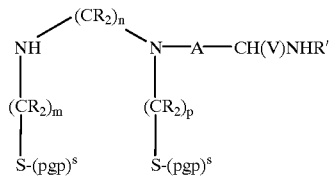

wherein each R is independently H, $CH_3$ or $C_2H_5$; m, n and p are independently 2 or 3; A is linear $C_1$–$C_8$ alkyl, substituted linear $C_1$–$C_8$ alkyl, cyclic $C_3$–$C_8$ alkyl, substituted cyclic $C_3$–$C_8$ alkyl, aryl, substituted aryl, or a combination thereof; V is H or CO-benzodiazepine; R' is H or benzodiazepine; provided that when V is H, R' is benzodiazepine and when R' is H, V is CO-benzodiazepine. In accordance with the invention, the substituted derivatives in the bisamide, bisthiol formulae are defined as set forth above.

Alternatively, the compound of the invention may comprise a metal ion chelator having a formula selected from the group consisting of:
diethylenetriaminepentaacetic acid (DTPA);
a derivative of DTPA having a formula $$(HOOCCH_2)_2N(CR_2)(CR_2)N(CH_2COOH)(CR_2)(CR_2)N(CH_2COOH)_2;$$

where each R is independently H, $C_1$ to $C_4$ alkyl, or aryl and one R is covalently linked to a bivalent linker;
ethylenediaminetetraacetic acid (EDTA);
a derivative of EDTA having a formula $$(HOOCCH_2)_2N(CR_2)(CR_2)N(CH_2COOH)_2;$$

where each R is independently H, $C_1$ to $C_4$ alkyl, or aryl and one R is covalently linked to a bivalent linker;
1,4,7,10-tetraazacyclododecanetetraacetic acid and derivatives thereof;
a metal ion chelator having a formula:

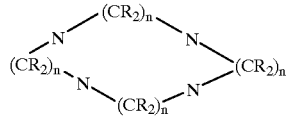

where n is an integer that is 2 or 3 and where each R is independently H, $C_1$ to $C_4$ alkyl, or aryl and one R is covalently linked to the benzodiazepine derivative, and desferrioxamine.

More preferably, the compounds of the invention comprise a monoamine, diamide, single thiol containing metal ion chelator such as those set forth in commonly assigned copending U.S. Ser. No. 08/253,973. Exemplary of such metal ion chelators are chelators having the formulae:

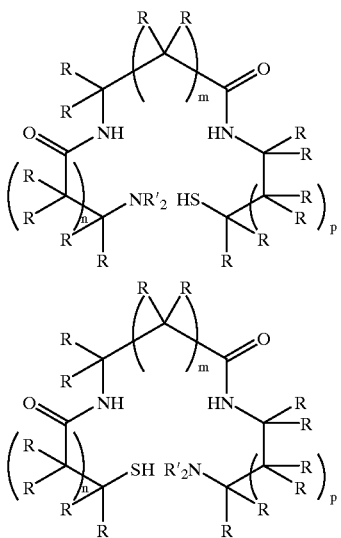

wherein n, m and p are each integers that are independently 0 or 1; each R' is independently H, lower alkyl, $C_2$–$C_4$ hydroxyalkyl, or $C_2$–$C_4$ alkoxyalkyl, and each R is independently H or R", where R" is a substituted $C_1$–$C_8$ alkyl not comprising a thiol group, a unsubstituted $C_1$–$C_8$ alkyl, an unsubstituted phenyl, or a substituted phenyl not comprising a thiol group, and one R or R' is $L^2$, where $L^2$ is a bivalent linker moiety linking the metal chelator to the glycoprotein IIb/IIIa receptor-binding benzodiazepine and wherein when one R' is $L^2$, $NR'_2$ is an amine. In this embodiment, $L^2$ may be a $C_1$–$C_6$ linear alkyl group, a branched chain alkyl group, a cyclic alkyl group, a carboxylic ester, a carboxamide, a sulfonamide, an ether, a thioether, an amine, an alkene, an alkyne, a 1,2-linked, optionally substituted, benzene ring, a 1,3-linked, optionally substituted, benzene ring, a 1,4-linked, optionally substituted, benzene ring, or an amino acid, or a combination thereof. In this embodiment, R" may be a $C_1$–$C_6$ linear alkyl group; a branched alkyl group; a cyclic alkyl group; a —$C_qOC_r$—, —$C_qNHC_r$— or —$C_qSC_r$— group, where q and r are integers each independently 1 to 5 wherein the sum of q+r is not greater than 6; ($C_1$–$C_6$) alkyl-X, where X is a hydroxyl group, a substituted amine, a guanidine, an amidine, a substituted thiol group, or a carboxylic acid, ester, phosphate, or sulfate group; a phenyl group or a phenyl group substituted with a halogen, a hydroxyl group, a substituted amine, a guanidine group, an amidine group, a substituted thiol, an ether, a phosphate, a sulfate; an indole group; a $C_1$–$C_6$ heterocyclic group containing 1 to 3 nitrogen, oxygen or sulfur atoms, or a combination thereof. In accordance with the invention, the substituted derivatives in the monoamine, diamide, thiol-containing chelator formulae are defined as set forth above.

Most preferably, the compounds of the invention comprise a metal ion chelator comprising a single thiol-containing group of formula:

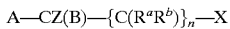

wherein A is H, HOOC—, $H_2$NOC—, —NHOC—, —OOC—, $R^e_2$NOC—, or $R^d$; B is H, SH, —$NHR^c$, —$N(R^c)$— or $R^d$; Z is H or $R^d$; X is SH, —$NHR^c$, —$N(R^c)$— or $R^d$; $R^a$, $R^b$, $R^c$ and $R^d$ are independently H, straight chain $C_1$–$C_8$ alkyl, branched chain $C_1$–$C_8$ alkyl, or cyclic $C_3$–$C_8$ alkyl; n is 0, 1 or 2; $R^e$ is $C_1$–$C_4$ alkyl, an amino acid, or a peptide comprising 2 to about 10 amino acids; and: (1) where B is —$NHR^c$ or —$N(R^c)$—, X is SH and n is 1 or 2; (2) where X is —$NHR^c$ or —$N(R^c)$—, B is SH and n is 1 or 2; (3) where B is H or $R^d$, A is HOOC—, $H_2$NOC—, —NHOC—, or —OOC—, X is SH and n is 0 or 1; (4) where A is H or $R^d$, then where B is SH, X is —$NHR^c$ or —$N(R^c)$— and where X is SH, B is —$NHR^c$ or —$N(R^c)$— and n is 1 or 2; (5) where X is H or $R^d$, A is HOOC—, $H_2$NOC—, —NHOC—, or —OOC—and B is SH; (6) where Z is methyl, X is methyl, A is HOOC—, $H_2$NOC—, —NHOC—, or —OOC— and B is SH and n is 0; and (7) where B is SH, X is not SH and where X is SH, B is not SH.

In accordance with the invention, a metal ion chelator comprising a single thiol-containing group may have the formula:

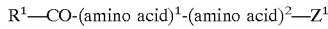

wherein (amino acid)$^1$ and (amino acid)$^2$ are each independently any primary α- or β-amino acid that does not comprise a thiol group, $Z^1$ is selected from the group consisting of cysteine, homocysteine, isocysteine, penicillamine, 2-mercaptoethylamine, 2-mercaptopropylamine, 2-mercapto-2-methylpropylamine, and 3-mercaptopropylamine, and $R^1$ is lower ($C^1$–$C^4$) alkyl, or $R^1$—CO is an amino acid, a peptide, or (aa)-peptide;
wherein when $Z^1$ is cysteine, homocysteine, isocysteine or penicillamine, $Z^1$ comprises a carbonyl group covalently linked to a hydroxyl group, a $NR^3R^4$ group, wherein each of $R^3$ and $R^4$ are independently H, a bond, lower ($C^1$–$C^4$) alkyl, an amino acid or a peptide comprising from 2 to 10 amino acids; and Alternatively, a metal ion chelator comprising a single thiol-containing group may have the formula:

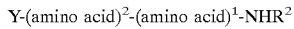

wherein (amino acid)$^1$ and (amino acid)$^2$ are each independently any primary α- or β-amino acid that does not comprise a thiol group Y is selected from the group consisting of cysteine, homocysteine, isocysteine, penicillamine, 2-mercaptoacetate, 2-mercaptopropionate, 2-mercapto-2-methylpropionate, 3-mercaptopropionate, and $R^2$ is H, a bond, lower ($C^1$–$C^4$) alkyl, and $NHR^2$ is an amino acid, a peptide, or (aa)-peptide;
wherein when Y is cysteine, homocysteine, isocysteine or penicillamine, Y comprises an amino group covalently linked to —H, an amino acid, a peptide, or (aa)-peptide.

Any naturally occurring, modified, substituted, or altered amino acid may be used in the single-thiol chelators of the invention. As used herein, the term "modified, substituted, or altered α- or β-amino acid" includes, without limitation, penicillamine (Pen); 6-aminocaproic acid (Aca); homolysine (Hly); L-{S-(3-aminopropyl)cysteine} (Apc); D-amino acids such as D-phenylalanine ($F_D$), D-tryptophan ($W_D$), D-tyrosine ($Y_D$), and the like; L-(4-chlorophenyl) alanine (Cpa); 4-amino-tetrahydrothiopyran-4-carboxylic acid (Thp); 2-naphthylalanine (Nal); D-2-naphthylalanine (D-Nal); dipropylglycine (Dpg); norleucine (Nle); homocysteine (Hcy); homohomocysteine (Hhc); aminoisobutyric acid (Aib); 2-aminoindan-2-carboxylic acid (Ain); 4-amino-cyclohexylalanine (Achxa); 4-aminomethyl-phenylalanine (Amf); S-(2-aminoethyl)cysteine (Aec); is O-(3- aminopropyl)serine (Aps); 2-aminobutyric acid (Abu); norvaline (Nva); 4-amidino-phenylalanine (Amp), 2-amino suberic acid (Asu), and the like. In accordance with the invention, the carboxyl terminal amino acids of the chelators of the invention may be in carboxylic acid form or in amidated form.

For example, suitable metal ion chelators may have any of the following formulae:

(amino acid)$^1$-(amino acid)$^2$-cysteine-,
(amino acid)$^1$-(amino acid)$^2$-isocysteine-,
(amino acid)$^1$-(amino acid)$^2$-homocysteine-,
(amino acid)$^1$-(amino acid)$^2$-penicillamine-,
(amino acid)$^1$-(amino acid)$^2$-2-mercaptoethylamine-,
(amino acid)$^1$-(amino acid)$^2$-2-mercaptopropyl amine-,
(amino acid)$^1$-(amino acid)$^2$-2-mercapto-2-methylpropylamine-,
(amino acid)$^1$-(amino acid)$^2$-3-mercaptopropylamine-, wherein the chelator is attached to either a substituted benzodiazepine or a linker group via a covalent bond with the carboxyl terminus of the chelator or a side chain on one of the amino acid groups.

Other suitable metal ion chelators include those selected from the group consisting of:

—cysteine-(amino acid)-($\alpha,\beta$- or $\beta,\gamma$-diamino acid);
—isocysteine-(amino acid)-($\alpha,\beta$- or $\beta,\gamma$-diamino acid);
—homocysteine-(amino acid)-($\alpha,\beta$- or $\beta,\gamma$-diamino acid);
—penicillamine-(amino acid)-($\alpha,\beta$- or $\beta,\gamma$-diamino acid);
2-mercaptoacetic acid-(amino acid)-($\alpha,\beta$- or $\beta,\gamma$-diamino acid);
2- or 3-mercaptopropionic acid-(amino acid)-($\alpha,\beta$- or $\beta,\gamma$-diamino acid);
2-mercapto-2-methylpropionic acid-(amino acid)-($\alpha,\beta$- or $\beta,\gamma$-diamino acid);

wherein the metal ion chelator is attached to either a substituted benzodiazepine or a linker group via a covalent bond with the amino terminus of the chelator or a side chain on one of the amino acid groups.

For example, the compounds of the invention may include metal ion chelators having a formula selected from the group consisting of: -Gly-Gly-Cys, -Gly-Gly-Cys.amide, Gly-Gly-Cys-, Cys-Gly-Gly-, -Gly-Gly-Gly-Cys (SEQ ID.NO: 1), -Gly-Gly-Gly-Cys.amide (SEQ.ID.NO: 1), Arg-Gly-Cys-, -($\epsilon$-Lys)-Gly-Cys-, -($\delta$-Orn)-Gly-Cys-, -($\gamma$-Dab)-Gly-Cys-, and -($\beta$-Dap)-Lys-Cys-, and the like. (In these formulae, it will be understood that $\epsilon$-Lys represents a lysine residue in which the $\epsilon$-amino group, rather than the typical $\alpha$-amino group, is covalently linked to the carboxyl group of the adjacent amino acid to form a peptide bond; $\delta$-Orn represents an ornithine residue in which the $\delta$-amino group, rather than the typical $\alpha$-amino group, is covalently linked to the carboxyl group of the adjacent amino acid to form a peptide bond; $\gamma$-Dab represents a 2,4-diaminobutyric acid residue in which the $\gamma$-amino group is covalently linked to the carboxyl group of the adjacent amino acid to form a peptide bond; and $\beta$-Dap represents a 1,3-diaminopropionic acid residue in which the $\beta$-amino group is covalently linked to the carboxyl group of the adjacent amino acid to form a peptide bond. Other abbreviations for amino acids are conventional. The designation "Cys.amide" represents the amidated form of the residue cysteine.)

Methods for making metal ion chelators of the most preferred embodiment are set forth in U.S. Pat. Nos. 5,443,815; 5,807,537; 5,814,297; and 5,866,097 and in U.S. Ser. Nos. 08/236,402; 08/253,678; 08/253,973; and 08/582,134.

Those of skill will recognize that most metal ions may be chelated to the above-mentioned metal ion chelators. Any metal ion capable of generating a signal label may be chelated to the benzodiazepine derivative compound of the invention, thus forming a metal ion complex with the compound of the invention. Suitable metal ions include radioactive metal ions, fluorescent metal ions, paramagnetic metal ions, heavy metals, rare earth ions suitable for use in computerized tomography, and the like. Radioactive metal ions or radionuclides are preferred. More preferably, $\gamma$-emitting radionuclides such as $^{67}$Cu, $^{68}$Ga, $^{111}$In, and $^{99m}$Tc, are used in the methods of the invention. Most preferably, complexes formed between, $^{99m}$Tc and the compounds of the invention are used to image thrombi.

The metal ion chelator associates with the metal ion to form a chelate, and the atoms of a chelator are commonly known as "ligands". In the chelating art, ligands are atoms capable of donating electrons to form the coordinate bonds of the chelate. In accordance with the invention, when the metal ion is $^{99m}$Tc, the chelate is termed a "$^{99m}$Tc-chelate". $^{99m}$Tc is a thiophilic metal, and thus the $^{99m}$Tc-chelates of the invention preferably contain at least one sulfur ligand bound via a coordinate covalent bond to the $^{99m}$Tc.

Complexes and chelates of the invention may be formed using known methods. For example, a salt of $^{99m}$Tc pertechnetate may be reacted with the compound in the presence of a reducing agent such as dithionite ions, stannous ions or ferrous ions. In this method, the most preferred reducing agent is stannous chloride. Alternatively, complexes and chelates may be formed by ligand exchange, wherein the compound of the invention is reacted with a pre-formed labile complex of $^{99m}$Tc and another compound known as a transfer ligand. In this process, any transfer ligand may be used, for example, tartrate, citrate, gluconate, glucoheptonate, or mannitol.

Thrombus imaging agents produced using the compounds of the invention are preferably administered intravenously to a living mammal, as pharmaceutical compositions. The compound of the invention is formulated as a sterile, pyrogen-free, parenterally acceptable aqueous solution which may optionally be supplied in lyophilized form and be reconstituted by the user.

The pharmaceutical composition of the invention comprise a compound of the invention in combination with a pharmaceutically acceptable diluent or a carrier such as species appropriate albumin. As used herein, a "pharmaceutically acceptable diluent or carrier" may include any and all solvents, dispersion media, antibacterial and antifungal agents, isotonic agents, enzyme inhibitors, stabilizers, and the like. The use of such media and agents for pharmaceutically active substances is well known in the art. For example, Sodium Chloride Injection and Ringer's Injection are commonly used as diluents. The preparation of such parenterally acceptable solutions, having due regard to pH, isotonicity, stability, and the like, is within the skill in the art.

The compounds and compositions of the invention may be provided as components of kits which may include buffers, additional vials, instructions for use, and the like. The kit of the invention comprises a sealed vial containing a predetermined quantity of the compound, and optionally, when the metal ion is technetium-99m, a reducing agent. An appropriate amount of a transfer ligand such as tartrate, citrate, gluconate, glucoheptonate or mannitol, for example, can also be included in the kit. The components of the kit may be in liquid, frozen or dry form. Preferably, kit components are provided in lyophilized form.

In accordance with the method of this invention, imaging agents produced from pharmaceutical compositions comprising the benzodiazepine derivative compounds of the invention are preferably administered intravenously in a single unit dose, either totally as a bolus or partly as a bolus followed by infusion over 1–2 hours. The amount of solution to be injected at unit dosage is from about 0.01 mL to about 10 mL, containing about 0.01 mCi to about 100 mCi of radioactivity, preferably from about 1 mCi to about 20 mCi. The amount of the compound in the unit dose may range from about 0.1 to about 10 mg/kg body weight, After intravenous administration, the thrombus site is monitored, for example, by radioimaging in vivo.

The following examples are shown by way of illustration and not by way of limitation.

EXAMPLE 1

Synthesis Of 1-[(carboxyglycyl-glycyl-glycyl-cysteinamide)methyl]-4-(2-carboxyethyl)-7-[(4-amidinophenyl)methyl]-3,4-dihydro-1H-1,4-benzodiazepine-2,5-dione Synthesis of an exemplary benzodiazepinedione imaging agent is set forth below.

A. N-Boc-5-hydroxyanthranilic acid [1]

5-Hydroxyanthranilic acid (100 g, 0.65 mol) was transferred into a 5 liter 3-necked round bottom flask equipped with a mechanical stirrer. A solution of saturated sodium carbonate (1.5 liters) was added to the reaction flask with stirring. After carbon dioxide evolution had subsided, di-t-butyldicarbonate (156.8 g, 0.72 mol) in 1.5 liters of tetrahydrofuran (THF) was added to the reaction vessel which was stirred at a rate which insured complete mixing of the resulting biphasic mixture. The reaction mixture was stirred at room temperature for 24 hours at which time 1.0 liters of ethyl ether was added and the mixture transferred to a separatory funnel. The aqueous layer was extracted with an additional 1.0 liters of ethyl ether and brought to pH=3.0 with 2 M $H_3PO_4$. Product was extracted from the aqueous solution with ethyl acetate (3×1.0 liters). The combined organics were washed with a saturated NaCl solution, dried over $Na_2SO_4$, filtered and concentrated in vacuo to yield N-Boc-5-hydroxyanthranilic acid (153 g, 92.5% yield).

B. N-Boc-5-benzyloxyanthranilic acid, benzyl ester [2]

Sodium hydride (95%, 36.2 g, 1.51 mol) was placed into a dry 5 liter 3-necked round bottom flask under an atmosphere of argon. Anhydrous dimethylformamide (DMF) (2.0 liters) was added via canula followed by the careful addition of N-Boc-5-hydroxyanthranilic acid (150 g, 0.59 mol). The reaction mixture was cooled with an ice/water bath and benzyl bromide (148 mL, 1.24 mol) was added via syringe keeping the reaction temperature below 50° C. After addition was complete, the reaction mixture was stirred at 45° C.–50° C. for 6 hours. At this time additional benzyl bromide (35 mL, 0.29 mol) was added and the reaction continued at 45° C.–50° C. for an additional 2 hours. Acetic acid (20 mL) was carefully added and the reaction mixture was transferred to a round bottom flask and concentrated to a volume of approximately 400 mL. Ethyl acetate (1.0 liters) was added and the resulting solution was decanted from any solids present. The flask was rinsed with additional ethyl acetate (2×500 mL), decanting after each rinse. The combined organics were washed with water (1.0 liter) and saturated NaCl (500 mL). The organics were filtered and concentrated in vacuo to yield crude N-Boc-5-benzyloxyanthranilic acid, benzyl ester as a reddish brown syrup. The crude product was transferred to boiling hexanes (3 liters) and refluxed an additional 10 minutes. The solution was filtered while still hot and allowed to cool for 48 hours to yield 72 g of product (28% yield).

C. 5-Benzyloxyanthranilic acid, benzyl ester, hydrochloride [3]

N-Boc-5-benzyloxyanthranilic acid, benzyl ester (70 g, 161 mmol) was added to a 1.4 M HCl/ethyl acetate solution (prepared by the addition of methanol to acetyl chloride and subsequent dilution with ethyl acetate). The reaction mixture was stirred at room temperature for 21 hours. After cooling to 0° C., the reaction was gently stirred for an additional 2 hours. The crystalline product was filtered off and washed with 50 ml of cold ethyl acetate. Trace solvents were removed under high vacuum to yield 5-benzyloxyanthranilic acid, benzyl ester, hydrochloride (53.4 g, 86% yield).

D. N-(Carbo-t-butoxymethyl)-5-benzyloxyanthranilic acid, benzyl ester [4]

A solution of saturated sodium bicarbonate (1.0 liter) was placed in a 4 liter Ehrlenmeyer flask along with 1.0 liter of ethyl acetate. The biphasic mixture was stirred at a rate that insured mixing and 5-benzyloxyanthranilic acid, benzyl ester, hydrochloride (50.0 g, 135 mmol) was added portionwise to the stirred mixture. After addition was complete, the mixture was stirred an additional 15 minutes. The layers were partitioned in a separatory funnel and the aqueous layer was extracted with ethyl acetate (500 mL). The combined organics were dried over $MgSO_4$, filtered, and concentrated in vacuo to yield the free base, which was dissolved in anhydrous DMF (700 mL) under an atmosphere of argon. 2,6-lutidine (20.0 mL, 172 mmol) was added to the solution followed by the addition of t-butyl bromoacetate (29.0 mL, 196 mmol). The reaction mixture was stirred at 70° C. under an atmosphere of argon for 48 hours. The DMF was removed on a rotary evaporator under high vacuum and the crude product residue was partitioned between ethyl acetate (1.0 liter) and water (500 mL). The organic layer was washed with saturated NaCl (250 mL) and dried over $Na_2SO_4$. The solution was filtered and concentrated in vacuo to yield crude product as a light brown solid. The product was recrystallized from 7% ethyl acetate/hexanes to yield N-(carbo-t-butoxymethyl)-5-benzyloxyanthranilic acid, benzyl ester (46.4 g, 79% yield).

E. N-(Carbo-t-butoxymethyl)-5-hydroxyanthranilic acid [5]

N-(Carbo-t-butoxymethyl)-5-benzyloxyanthranilic acid, benzyl ester (45.0 g, 101 mmol) was dissolved in 1:1 THF/ethyl acetate (1200 mL) in a 2 liter round bottom flask. The atmosphere was flushed with argon and 10% Pd/C (4.0 g) was added. The reaction atmosphere was replaced with hydrogen gas (4 purge-fill cycles) and the reaction mixture stirred under a balloon of hydrogen for 23 hours. The atmosphere was replaced with argon and the reaction mixture filtered through a pad of Celite, washing the Celite pad with methanol (250 mL). The solvents were removed in vacuo and the resulting yellow solid placed under high vacuum overnight to yield N-(carbo-t-butoxymethyl)-5-hydroxyanthranilic acid (27.1 g, 100% yield).

F. N-(Carbobenzyloxymethyl)-3-aminopropionic acid, ethyl ester [6]

Ethyl acrylate (24.4 mL, 225 mmol) and glycine, benzyl ester, p-toluenesulfonate (50.0 g, 148 mmol) were combined in a 250 mL round bottom flask. With stirring, triethylamine (24.8 mL, 178 mmol) was added via syringe and the reaction mixture was stirred at room temperature for 22 hours. The reaction mixture was partitioned between ethyl acetate (660 mL) and 10% aqueous $Na_2CO_3$ (300 mL). The organics were washed with water (100 mL) and saturated NaCl (100 mL). The organics were dried over $MgSO_4$, filtered and concentrated in vacuo followed by pumping under high vacuum to yield N-(carbobenzyloxymethyl)-3-aminopropionic acid, ethyl ester (39.3 g, 73% yield) as a yellow oil.

F. 1-(Carbo-t-butoxymethyl)-4-(2-carboethoxyethyl)-7-hydroxy-3,4-dihydro-1H-1,4-benzodiazepine-2,5-dione [7]

N-(Carbo-t-butoxymethyl)-5-hydroxyanthranilic acid (26.7 g, 100 mmol) was placed in a dry 2 liter round bottom flask. The reaction atmosphere was flushed with argon and N-(carbobenzyloxymethyl)-3-aminopropionic acid, ethyl ester (29.0 g, 109 mmol) in anhydrous DMF (500 mL) was added, followed by the addition of O-(7-azabenzotriaol-1-yl)-1,1,3,3-tetramethyluronium hexafluorophosphate (HATU reagent, 39.9 g, 105 mmol). Triethylamine (42.0 mL, 301 mmol) was added and the reaction mixture was stirred at room temperature under a balloon of argon for 16 hours. The DMF was removed in vacuo on a rotary evaporator and the residue partitioned between ethyl acetate (1.0 liter) and saturated NaHCO$_3$ (500 mL). The organics were washed with water (500 mL), saturated NaCl (100 mL) and dried over MgSO$_4$. The organics were filtered, the volatiles removed in vacuo on a rotary evaporator and the residual oil pumped on under high vacuum to yield an oil. This oil was taken up in 9:3 ethyl acetate/methanol (1200 mL) and placed under an atmosphere of argon gas. 10% Pd/C (4.0 g) was added and the reaction atmosphere replaced with hydrogen gas (4 purge-fills). The reaction mixture was stirred under a balloon of hydrogen for 45 hours. The reaction atmosphere was replaced with argon and the suspension filtered through a pad of Celite, which was washed with an additional 300 mL of methanol. The volatiles were removed in vacuo and the residue was taken up in a minimum of dichloromethane and chromatographed on silica gel, eluting the column with 1:1 ethyl acetate/hexanes. Fractions containing pure product (Rf=0.17 in 1:1 ethyl acetate/hexanes) were combined and the solvents removed in vacuo to yield 1-(carbo-t-butoxymethyl)-4-(2-carboethoxyethyl)-7-hydroxy-3,4-dihydro-1H-1,4-benzodiazepine-2,5-dione as a white solid (20.2 g, 50% yield).

G. 1-(Carbo-t-butoxymethyl)-4-(2-carboethoxyethyl)-7-[(4-cyanophenyl)methyl]-3,4-dihydro-1H-1,4-benzodiazepine-2,5-dione [8]

1-(Carbo-t-butoxymethyl)-4-(2-carboethoxyethyl)-7-hydroxy-3,4-dihydro-1H-1,4-benzodiazepine-2,5-dione (19.5 g, 48 mmol), α-bromo-p-tolunitrile (11.3 g, 58 mmol), and potassium carbonate (9.0 g, 65 mmol) were combined in a round bottom flask. Anhydrous DMF (300 mL) was added and the reaction mixture was stirred at 40° C. for 4 days. The reaction mixture was filtered and the filtrate was concentrated in vacuo on a rotary evaporator. The residue was partitioned between ethyl acetate (500 mL) and water (100 mL). The organics were washed with saturated NaCl (50 mL) and dried over Na$_2$SO$_4$. The volatiles were removed in vacuo on a rotary evaporator and the residue was chromatographed on silica gel, eluting the column with 5:6 ethyl acetate/hexanes. Fractions containing pure product (Rf=0.17, 5:6 ethyl acetate/hexanes) were combined and the solvents removed in vacuo on a rotary evaporator to yield 1-(carbo-t-butoxymethyl)-4-(2-carboethoxyethyl)-7-[(4-cyanophenyl)methyl]-3,4-dihydro-1H-1,4-benzodiazepine-2,5-dione (20.7 g, 83% yield).

H. 1-(Carbo-t-butoxymethyl)-4-(2-carboethoxyethyl)-7-[(4-amidinophenyl)methyl]-3,4-dihydro-1H-1,4-benzodiazepine-2,5-dione, acetate [9]

1-(Carbo-t-butoxymethyl)-4-(2-carboethoxyethyl)-7-[(4-cyanophenyl)methyl]-3,4-dihydro-1H-1,4-benzodiazepine-2,5-dione (16.0 g, 31 mmol) was placed in a dry 3-necked flask equipped with an inlet tube for gas dispersion and an outlet tube connected to a trap containing 1:1 2M NaOH/Clorox bleach. The flask was flushed with argon gas and anhydrous pyridine (90 mL) was added followed by the addition of triethylamine (70 mL). The resulting solution was saturated with hydrogen sulfide gas. The inlet and outlet tubes were removed and the reaction mixture was heated at 55° C.–60° C. for 21 hours. The reaction mixture was purged with argon and the volatiles removed in vacuo on a rotary evaporator. The residue was taken up in 5:4 dichloromethane/toluene (450 mL) and this was also removed in vacuo on a rotary evaporator. The treatment with dichloromethane/toluene was repeated once more. The residue was taken up in acetone (300 mL) and iodomethane (5.2 mL, 84 mmol) was added via syringe. The reaction mixture was stirred and heated at 60° C.–65° C. for 5.5 hours. The reaction mixture was cooled and the volatiles removed in vacuo on a rotary evaporator. The residue was taken up in anhydrous methanol (200 mL) under and atmosphere of argon and ammonium acetate (9.25 g, 120 mmol) was added. The reaction mixture was stirred at room temperature under an atmosphere of argon for 21 hours. The volatiles removed in vacuo on a rotary evaporator and the residue was taken up in acetonitrile (200 mL) and filtered through a sintered glass funnel. The reaction vessel was rinsed with additional acetonitrile (100 mL) which was also filtered through the sintered glass funnel. The filtrate was concentrated in vacuo on a rotary evaporator and the residue pumped on under high vacuum to yield 1-(carbo-t-butoxymethyl)-4-(2-carboethoxyethyl)-7-[(4-amidinophenyl)methyl]-3,4-dihydro-1H-1,4-benzodiazepine-2,5-dione, acetate (18.2 g, 99% yield)

I. 1-(Carboxymethyl)-4-(2-carboethoxyethyl)-7-[(4-amidinophenyl)methyl]-3,4-dihydro-1H-1,4-benzodiazepine-2,5-dione, hydrochloride [10]

1-(carbo-t-butoxymethyl)-4-(2-carboethoxyethyl)-7-[(4-amidinophenyl)methyl]-3,4-dihydro-1H-1,4-benzodiazepine-2,5-dione, acetate (17.7 g, 30 mmol) was placed in a dry round bottom flask and 4M HCl/dioxane was added via syringe. The reaction mixture was stirred at room temperature for 1.5 hours and then added dropwise to a stirred solution of anhydrous ethyl ether (1.0 liter). After addition was complete, the resulting suspension was stirred an additional 15 minutes and filtered under a blanket of argon gas. The collected solid was washed with anhydrous ethyl ether, transferred to a round bottom flask, and dried under high vacuum to yield 1-(carboxymethyl)-4-(2-carboethoxyethyl)-7-[(4-amidinophenyl)methyl]-3,4-dihydro-1H-1,4-benzodiazepine-2,5-dione, hydrochloride as a white solid (14.2 g, 93% yield). $^1$H NMR (CD$_3$OD): 1.25 ppm, (t, 3H); 2.70 ppm, (m, 2H); 3.70 ppm–4.21 ppm, (m, 4H); 4.12 (q, 2H); 4.50 ppm, (s, 2H); 5.39 ppm, (s, 2H); 7.20 ppm–7.40 ppm (m, 3H); 7.71 ppm (d, 2H); 7.83 ppm (d, 2H).

J. Fmoc-Glycyl-glycyl-glycyl-S-Tritylcysteinyl-Rink amide resin [11]

Fmoc-Rink amide resin (12.5 g, 0.66 mmol/g, 8.25 mmol) was sequentially coupled to N-Fmoc-S-tritylcysteine, Fmoc-glycine, Fmoc-glycine, Fmoc-glycine, and Fmoc-glycine using the following solid-phase peptide synthesis protocol: The N-terminal Fmoc group was removed by treatment of the resin with 20% piperidine/DMF (2 times, 5 min. then 15 min.). The resin was washed with DMF (4×1 min.). The resulting resin-supported N-terminal free amine was suspended in DMF and reacted with N-Fmoc-S-tritylcysteine (13.7 g, 23.4 mmol), which was preactivated with a 0.45M solution of 1:1 2-(1H-benzotriazole-1-yl)-1,1,3,3,-tetramethyluronium hexafluorophosphate/N-hydroxybenzotriazole (HBTU/HOBt) in DMF (52 mL, 23.4 mmol) and diisopropylethylamine (8.3 mL, 47.6 mmol). The reaction time was for 2 hours. The resin was washed with DMF (3 times), dichloromethane (3 times), and DMF (3 times). Fmoc-glycine (7.0 g, 23.5 mmol) was similarly reacted with the resin supported peptide in three sequential procedures to produce Fmoc-glycyl-glycyl-glycyl-S-tritylcysteinyl-Rink amide resin. The resin was washed with dichloromethane (3 times) and dried in vacuo. Substitution analysis on a small portion of resin indicated that resin substitution was 0.13 mmol/g.

K. 1-[(Carboxyglycyl-glycyl-glycyl-S-tritylcysteinamide) methyl]-4-(2-carboethoxyethyl)-7-[(4-amidinophenyl) methyl]-3,4-dihydro-1H-1,4-benzodiazepine-2,5-dione, trifluoroacetate [12]

Fmoc-glycyl-glycyl-glycyl-S-tritylcysteinyl-Rink amide resin (53.4 g, 6.94 mmol) was treated (2 times) with 20% piperidine/DMF (75 mL, 5 min. then 15 min.) and washed with DMF (4 times). Separately, 1-(carboxymethyl)-4-(2-carboethoxyethyl)-7-[(4-amidinophenyl)methyl]-3,4-dihydro-1H-1,4-benzodiazepine-2,5-dione, hydrochloride (5.9 g, 11.36 mmol) was placed in a dry round bottom flask under an atmosphere of argon and dissolved in anhydrous DMF (75 mL). This solution was stirred and cooled to 0° C. and treated with 4-methylmorpholine (1.01 mL, 9.2 mmol) followed by the dropwise addition of isobutyl chloroformate (1.13 mL, 8.7 mmol). After addition was complete, the solution was stirred at 0° C. for an additional 5 minutes and added to the resin-supported peptide free amine that was generated above. The resin suspension was agitated for 3 hours. The resin was washed with DMF (6 times) and dichloromethane (3 times). The resin was treated three times with trifluoroacetic acid (40 mL) for 10 minutes, each time draining the deprotection mixture into a round bottom flask. The resin was washed twice with dichloromethane (75 mL). The dichloromethane washes were combined with the trifluoroacetic acid deprotection mixtures and the volatiles removed in vacuo on a rotary evaporator. The residue was treated with anhydrous chloroform several times, each time removing the chloroform in vacuo on a rotary evaporator. This is done until the orange/yellow color of the residue disappears, indicating reattachment of the trityl group to the cysteine sulfhydryl. The crude product was pumped on under high vacuum to yield 1-[(carboxyglycyl-glycyl-glycyl-S-tritylcysteinamide)methyl]-4-(2-carboethoxyethyl)-7-[(4-amidinophenyl)methyl]- 3,4-dihydro-1H-1,4-benzodiazepine-2,5-dione, trifluoroacetate (8.4 g). The product was purified by reversed-phase C18 HPLC. The column was loaded with a DMF solution of crude product (70 mg/mL) and eluted with a linear gradient of 0.1% TFA in 90% acetonitrile/water (solvent B) and 0.1% TFA in water (solvent A). The gradient was from 20% B/A to 45% B/A over 40 minutes. Fractions were analyzed by reversed-phase C18 HPLC and fractions containing pure product were combined and lyophilized to yield 1-[(carboxyglycyl-glycyl-glycyl-S-tritylcysteinamide) methyl]-4-(2-carboethoxyethyl)-7-[(4-amidinophenyl) methyl]-3,4-dihydro-1H-1,4-benzodiazepine-2,5-dione, trifluoroacetate as a white powder (2.41 g, 2.17 mmol, 31% yield). Electrospray mass spectral analysis indicated a molecular ion peak (M+H$^+$) of 998 (theoretical for $C_{52}H_{56}N_9O_{10}S_1$ is 998.4).

L. 1-[(Carboxyglycyl-glycyl-glycyl-cysteinamide)methyl]-4-(2-carboxyethyl)-7-[(4-amidinophenyl)methyl]-3,4-dihydro-1H-1,4-benzodiazepine-2,5-dione, trifluoroacetate [13]

1-[(carboxyglycyl-glycyl-glycyl-S-tritylcysteinamide) methyl]-4-(2-carboethoxyethyl)-7-[(4-amidinophenyl) methyl]-3,4-dihydro-1H-1,4-benzodiazepine-2,5-dione, trifluoroacetate (2.38 g, 2.14 mmol) was placed in a round bottom flask and dissolved in methanol (100 mL). The stirred solution was treated with an aqueous solution of 1.0 M lithium hydroxide (8.7 mL, 8.7 mmol) at room temperature for 20 hours. Trifluoroacetic acid (0.67 mL, 8.7 mmol) was added to quench the reaction and the volatiles were removed in vacuo on a rotary evaporator. The residue was treated with a 91:4:5 mixture of trifluoroacetic acid/triethylsilane/water (100 mL) for 45 minutes. The volatiles were removed in vacuo on a rotary evaporator. The residue was dissolved in 0.1% TFA in 90% acetonitrile/water (20 mL) and the stirred solution was diluted with 0.1% TFA in water (200 mL). The resulting precipitate was filtered off through a pad of Celite, which was washed with additional 0.1% TFA in water (100 mL). The combined filtrates were purified (in portions) by preparative reversed-phase C18 HPLC. The column was eluted with a linear gradient of 100% A to 15% B/A over 40 minutes (0.1% TFA in water is solvent A and 0.1% TFA in 90% acetonitrile/water is solvent B). Fractions were analyzed by reversed-phase C18 HPLC and fractions containing pure product were combined and lyophilized to yield 1-[(carboxyglycyl-glycyl-glycyl-cysteinamide)methyl]-4-(2-carboxyethyl)-7-[(4-amidinophenyl)methyl]-3,4-dihydro-1H-1,4-benzodiazepine-2,5-dione, trifluoroacetate as a white powder (1.08 g, 12.4 mmol, 58 % yield).

EXAMPLE 2

Placebo Vial Method for Radiolabeling with Technetium-99m

Approximately 100 μg of the benzodiazepine derivative compound of Example 1 as 100 μL of a 1 mg/mL TFA salt solution dissolved in 0.9% saline was added to a "placebo vial", containing lyophilized 5 mg sodium glucoheptanate dihydrate, 50 μg stannous chloride dihydrate, and 100 μg sodium edetate dihydrate. The vial was then reconstituted with $^{99m}$Tc-sodium pertechnetate (30 to 50 mCi) and saline such that the total volume was 1.1 mL. Following reconstitution, the vials were incubated at room temperature for 30 minutes.

The purity of the $^{99m}$Tc-labeled benzodiazepinedione derivative was determined by reverse-phase analytical HPLC using the following conditions: a Waters Delta Pak C18, 5 μ, 3.9 mm×150 mm analytical column was loaded with each radiolabeled peptide, and the peptides eluted at a solvent flow rate equal to 1.2 mL/min. Gradient elution was performed using a linear gradient of 12–25% Solvent B/Solvent A (Solvent A is 0.1% (v/v) trifluoroacetic acid (TFA) in water and Solvent B is 0.1% (v/v) TFA in 90/10 (v/v) acetonitrile/water) over 20 minutes; followed by a linear gradient of 25–100% Solvent B/Solvent A over four minutes and 100% Solvent B/Solvent A for three minutes (Method 1).

Radioactive components were detected in the HPLC method using an in-line radiometric detector linked to a computerized data collection and analysis system (Waters Millenium). $^{99m}$Tc-glucoheptate, $^{99m}$Tc-edetate, and $^{99m}$Tc-sodium pertechnetate elute between one and four minutes under these conditions, whereas the $^{99m}$Tc-labeled benzodiazepinedione derivatives eluted after a much greater time. The radiochemical purity (as determined by the % area of the main $^{99m}$Tc product peaks) was ≧90%.

The purity of the $^{99m}$Tc-labeled benzodiazepinedione derivative was also determined by TLC quality control analysis. The radiolabeled peptide samples were spotted at the origin of each of two Gelman ITLC-SG strips. One strip each was developed in saturated saline (SAS) and 1:1 (v:v) methanol:0.1 M ammonium acetate (MAM) and allowed to dry. The SAS strips were cut at $R_f$ 0.75 and the MAM strip was cut at $R_f$ 0.40. The portions of the strips were counted for radioactivity in a dose calibrator, and the per cent activity of the top and bottom portions of each strip calculated. The radiochemical purity of each sample was calculated as follows:

Purity by TLC=% bottom (SAS)−% bottom (MAM)

The radiochemical purity by TLC was ≧90%.

EXAMPLE 3

Formulated Kit Method for Radiolabeling with Technetium-99m

Formulated kits were prepared by combining components in an appropriate ratio in aqueous solution, adjusting the pH to pH 7.4, dispensing 1.0 mL into glass vials, and lyophilizing. The components were dissolved in aqueous solution such that one milliliter (one vial) contained the following: 50 μg of the benzodiazepinedione derivative of Example 1 with 25 mg sodium glucoheptonate dihydrate, 50 μg stannous chloride dihydrate, 100 μg sodium edetate dihydrate, and 5 mg L-methionine. The formulated kit was reconstituted with $^{99m}$Tc-sodium pertechnetate (45 to 55 mCi) and saline such that the total volume was 1.0 mL. Following reconstitution, the formulated kit vials were incubated at 100° C. in a boiling water bath for 10 minutes, and allowed to cool for 20 minutes at room temperature.

The purity of the $^{99m}$Tc-labeled benzodiazepinedione derivative was determined by reverse-phase analytical HPLC using the following conditions: a Zorbax 300SB C18, 4 μ, 4.6 mm×250 mm analytical column was loaded with each radiolabeled peptide, and the peptides eluted at a solvent flow rate equal to 1.2 mL/min. Gradient elution was performed using a linear gradient of 23–46% Solvent D/Solvent C (Solvent C is 5 mM tetrabutylammonium phosphate pH 7.5 in water and Solvent D is 5 mM tetrabutylammonium phosphate pH 7.5 in 60/40 acetonitrile/water) over 20 minutes; followed by a linear gradient of 46–100% Solvent D/Solvent C over 5 minutes and 100% Solvent D/Solvent C for 5 minutes (Method 2).

Radioactive components were detected in HPLC Method 2 by the same detection methods described for Method 1 in Example 2. The radiochemical purity obtained from the formulated kit preparations (as determined by the % area of the main $^{99m}$Tc product peaks) was ≧90% for >6 hours.

The purity of the $^{99m}$Tc-labeled benzodiazepinedione derivative was also determined by TLC quality control analysis as described in Example 2.

Results of HPLC and TLC analysis of the $^{99m}$Tc-labeled benzodiazepinedione derivative synthesized in Example 1 are shown in Table 1.

TABLE 1

TLC and HPLC Results for $^{99m}$Tc-Labeled Benzodiazepinedione

|  | TLC Purity (%) | HPLC Method | HPLC Retention Time (min) | HPLC Purity (%) |
| --- | --- | --- | --- | --- |
| Example 2 | 99 | 1 | 10.8, 12.0 | 92 |
| Example 3[a] | 99 | 2 | 11.8, 13.7 | 94 |
|  | 100 | 2 | 11.6, 13.5 | 94 |

[a]Two entries represent two different lots of formulated kits.

EXAMPLE 4

In vitro Studies $^{99m}$Tc-benzodiazepinedione derivative was prepared as described in Example 2.

Preparation of Platelet-Rich Plasma (PRP). In all experiments, platelets were isolated on the day of the experiment from citrated human blood. After obtaining informed consent, 27 mL of blood was withdrawn from the antecubital vein of healthy adult volunteers into a polypropylene syringe containing 3 mL of sodium citrate (3.8% w/v, pH 7.4). Universal precautions for handling biological fluids were followed. Citrated blood was transferred to a 50 mL conical centrifuge tube and centrifuged at 900 rpm (160×g) for 10 minutes to obtain PRP.

Washed Platelets. Washed platelets were prepared by centrifuging PRP at 2,200 rpm (1,400×g) for 12 min. The platelet-poor plasma (PPP) was decanted and the resulting pellet suspended in modified Tyrodes buffer. The PPP was decanted and discarded. Modified Tyrodes buffer (0.8 mL per mL of original PRP) was immediately layered over the platelet pellet and prostaglandin $E_1$ ($PGE_1$; 1 μL of a 40 μM solution per mL of Tyrodes buffer) added to prevent platelet activation. (McLane M A, Kowalska M A, Silver L, Shattil S J and Niewiarowski S. (1994) *Biochem J* 301: 429–426). The pellet was resuspended with a plastic Pasteur pipette. The centrifugation step was repeated to wash the platelets that were diluted in 150 mL of Tyrodes buffer for binding assays.

Polyethyleneimine-Treated Filters. The filters (GF/C) were presoaked in 10 mM Tris-HCl (pH 9.1) polyethyleneimine (0.5%) and P829 (0.001%) for at least one hour prior to assay to decrease the nonspecific binding of $^{99m}$Tc labeled benzodiazepinedione derivative to the filter.

Binding of $^{99m}$Tc-benzodiazepinedione derivative to Washed Platelets. Platelets (125 μL) were incubated in silanized glass tubes for 60 min at 37° C. in a shaking water bath in a total volume of 250 μL of Tyrodes buffer containing $^{99m}$Tc-benzodiazepinedione derivative (50, 30, 10, 7, 5, 3, 1, 0.7, 0.5, 0.3, 0.1, and 0.07 nM final concentration). To determine the binding of $^{99m}$Tc-benzodiazepinedione derivative to "activated" platelets, a 10 μL aliquot of a 0.5 mM solution of ADP (20 μM final concentration), and a 10 μL aliquot of a 1:1 mixture of 250 mM $CaCl_2$ and $MgCl_2$ was added to appropriate tubes. Nonspecific binding was determined by the addition of excess unlabeled benzodiazepinedione derivative (100 μM) to fully saturate the GPIIb/IIIa receptor. The $^{99m}$Tc-benzodiazepinedione derivative bound to the platelets was separated from the free $^{99m}$Tc-benzodiazepinedione derivative by filtration through treated GF/C Glass Fiber Filters (Cat. No. FP24-GF/C, Brandel, Gaithersburg, Md.) using a Brandel Cell harvester (Cat. No. SM24T Brandel, Gaithersburg Md.) connected to a vacuum source (15 to 20 mm Hg). Filters were then washed with 9 mL of 10 mM Tris-HCl buffer at pH 7.8 (4° C.) and counted for radioactivity in a gamma counter.

Calculations. The specific binding of $^{99m}$Tc-benzodiazepinedione derivative was calculated by subtracting the nonspecific binding in the presence of excess unlabeled benzodiazepinedione derivative from the total binding measured in the absence of excess benzodiazepinedione derivative. The data were plotted as a Scatchard Plot as described in Bylung D B and Yamamura H I, *Methods for receptor binding*, Ravens Press Ltd. (New York. 1990) pp. 1–32. The data points were fitted with the linear regression function in the KaleidaGraph (Synergy Software Inc.) software package. The $K_d$ values were calculated as the negative reciprocal of the slope.

Statistics. Each response variable was compared between the two factor levels in each of the two factors using a paired student's t-test from the Instat Program (GraphPad Software, San Diego, Calif.). The threshold p value was set to 0.05 for rejection of the null hypothesis. For the Response Variable: $K_d$; Level 1: Basal (no ADP); Level 2: Activated (ADP), factor levels were compared in platelets isolated from the same individual. Experiments were run simultaneously. The platelets from four subjects were used.

The average $K_d$ for the binding of $^{99m}$Tc-benzodiazepinedione derivative to resting and activated human platelets was 30.5 nM and 13.5 nM, respectively. Thus, more $^{99m}$Tc-benzodiazepinedione derivative bound to activated platelets. The average fold-increase in binding to activated platelets over all concentrations tested was 1.8, and ranged from 1.2 to 2.3 fold. The data obtained from Scatchard plots from which the $K_d$ values were derived are summarized in Table 2.

TABLE 2

Kd Values for Binding to Human Platelets (nM).

| | Technetium Tc 99m P424 | |
|---|---|---|
| | Basal | ADP |
| Subject 1 | 32 | 15 |
| Subject 2 | 20 | 12 |
| Subject 3 | 47 | 20 |
| Subject 4 | 23 | 7 |
| Mean | 30.5 ± 6 | 13.5 ± 3 |

These data demonstrate that a $^{99m}$Tc-benzodiazepinedione derivative produced in accordance with the invention binds with higher potency to activated platelets than to resting platelets.

EXAMPLE 5

In Vivo Imaging of Deep Vein Thrombosis using a $^{99m}$Tc-Labeled Benzodiazepinedione Derivative in a Canine Model Three mongrel dogs (25–35lb., fasted overnight) were sedated with a combination of ketamine and aceprozamine intramuscularly and then anesthetized with sodium pentabarbital intravenously. In each animal, an 18-gauge angiocath was inserted in the distal half of the right femoral vein and an 8 mm Dacron®-entwined stainless steel embolization coil (Cook Co., Bloomington Ind.) was placed in the femoral vein at approximately mid-femur. The catheter was removed, the wound sutured and the placement of the coil documented by X-ray. The animals were then allowed to recover overnight.

One day following coil placement, each animal was re-anesthetized, intravenous saline drips placed in each foreleg and a urinary bladder catheter inserted to collect urine. The animal was placed supine under a gamma camera which was equipped with a low-energy, all purpose collimator and photopeaked for $^{99m}$Tc.

The benzodiazepinedione derivative of Example 1 was labeled with $^{99m}$Tc [185–370 mBq (5–10 mCi)] and injected sequentially into one foreleg intravenous line at its point of insertion. The second line was maintained for blood collection.

Gamma camera imaging was started simultaneously with injection. Anterior images over the heart were acquired as a dynamic study (10 second image acquisitions) over the first 10 minutes, and then as static images at 1, 2, 3 and 4 hours post-injection. Anterior images over the legs were acquired for 500,000 counts or 20 minutes (whichever was shorter), at approximately 10–20 minutes, and at approximately 1, 2, 3 and 4 hours post-injection. Leg images were collected with a lead shield placed over the bladder.

Following the final image, each animal was deeply anesthetized with pentobarbital. Two blood samples were collected on a cardiac puncture using a heparinized syringe followed by a euthanizing dose of saturated potassium chloride solution administered by intercardiac or bolus intravenous injection. The femoral vein containing the thrombus, a similar section of vein of the contralateral (control) leg, sections of the vessel proximal to the thrombus and samples of thigh muscle were then carefully dissected out. The thrombus, coil and coil Dacron fibers were then dissected free of the vessel. The thrombus, saline-washed vessel samples, coil and coil Dacron fibers were separated, and each sample was placed in a pre-weighed test tube. The samples were weighed and counted in a gamma well counter in the Tc-99 m channel, along with known fractions of the injected doses.

Fresh thrombus weight, percent injected dose (%ID)/g in the thrombus and blood obtained just prior to euthanasia and thrombus/blood and thrombus/muscle ratios were determined. From the computer-stored images, thrombus/background ratios were determined by analysis of the counts/pixel measured in regions-of-interest (ROD drawn over the thrombus and adjacent muscle. Tissue data from these experiments are shown in Table 3.

TABLE 3

Canine Model of Pulmonary Embolism and Deep Vein Thrombosis[1]

| | Leg Thrombus | Lung Thrombus |
|---|---|---|
| Thrombus/Background[2] | 4.2 (n = 2) | 1.3 (n = 1) |
| % ID/g Thrombus | 0.050 ± 0.020 | 0.15 ± 0.048 |
| Thrombus/Blood[3] | 9.1 ± 4.6 | 27 ± 9 |
| Thrombus/Muscle[3] | 30 ± 15 | — |
| Thrombus/Normal Lung[3] | — | 29 ± 9 |
| Thrombus Weight | 430 ± 210 mg | 30 ± 15 mg |

[1]Mean ± standard deviation
[2]From analysis of image regions of interest
[3]Ratio of % injected dose/g (% ID/g)

These results demonstrate that pulmonary emboli and deep vein thrombi can be rapidly and efficiently located in vivo using Tc-99 m labeled benzodiazepinedione derivatives of the invention.

It should be understood that the foregoing disclosure emphasizes certain specific embodiments of the invention and that all modifications or equivalents thereto are within the spirit and scope of the invention as set forth in the appended claims.

What is claimed is:

1. A compound comprising a glycoprotein IIb/IIIa receptor binding benzodiazepine moiety covalently linked to a metal ion chelator, wherein the compound has an $IC_{50}$ for inhibition of human platelet aggregation of less than about 1 $\mu$M, as measured in a standard inhibition of platelet aggregation assay.

2. The compound of claim 1, having a formula:

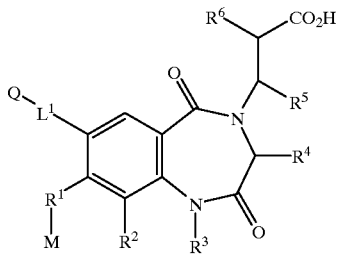

where $R^1$ is $C_1$–$C_8$ lower alkyl, $R^2$, $R^3$, $R^4$, $R^5$, and $R^6$ are each independently H, $C_1$–$C_8$ lower alkyl, substituted alkyl, aryl, substituted aryl, or a combination thereof; $L^1$ is a linking moiety; Q is a positively charged nitrogen-containing moiety; and M is a metal ion chelator.

3. The compound of claim 1, having a formula:

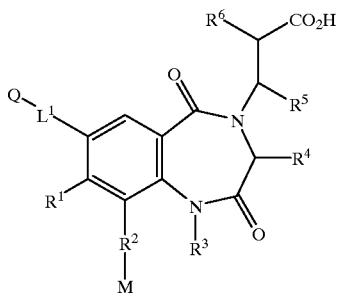

where $R^2$ is $C_1$–$C_8$ lower alkyl, $R^1$, $R^3$, $R^4$, $R^5$, and $R^6$ are each independently H, $C_1$–$C_8$ lower alkyl, substituted alkyl, aryl, substituted aryl, or a combination thereof; $L^1$ is a linking moiety; Q is a positively charged nitrogen-containing moiety; and M is a metal ion chelator.

4. The compound of claim 1, having a formula:

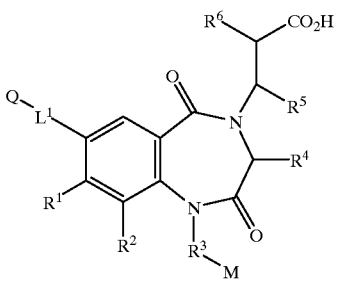

where $R^3$ is $C_1$–$C_8$ lower alkyl; $R^1$, $R^2$, $R^4$, $R^5$, and $R^6$ are each independently H, $C_1$–$C_8$ lower alkyl, substituted alkyl, aryl, substituted aryl, or a combination thereof; $L^1$ is a linking moiety; Q is a positively charged nitrogen-containing moiety; and M is a metal ion chelator.

5. The compound of claim 1, having a formula:

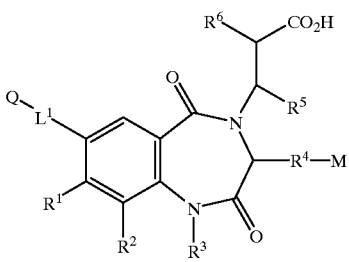

where $R^4$ is $C_1$–$C_8$ lower alkyl; $R^1$, $R^2$, $R^3$, $R^5$, and $R^6$ are each independently H, $C_1$–$C_8$ lower alkyl, substituted alkyl, aryl, substituted aryl, or a combination thereof; $L^1$ is a linking moiety; Q is a positively charged nitrogen-containing moiety; and M is a metal ion chelator.

6. The compound of claim 1, having a formula:

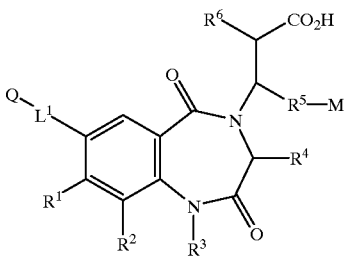

where $R^5$ is $C_1$–$C_8$ lower alkyl; $R^1$, $R^2$, $R^3$, $R^4$, and $R^6$ are each independently H, $C_1$–$C_8$ lower alkyl, substituted alkyl, aryl, substituted aryl, or a combination thereof; $L^1$ is a linking moiety; Q is a positively charged nitrogen-containing moiety; and M is a metal ion chelator.

7. The compound of claim 1, having a formula:

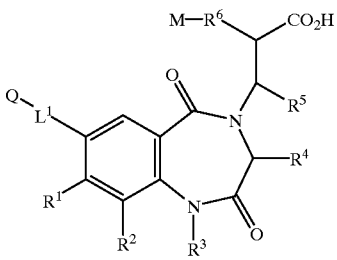

where $R^6$ is $C_1$–$C_8$ lower alkyl; $R^1$, $R^2$, $R^3$, $R^4$, and $R^5$ are each independently H, $C_1$–$C_8$ lower alkyl, substituted alkyl, aryl, substituted aryl, or a combination thereof; $L^1$ is a linking moiety; Q is a positively charged nitrogen-containing moiety; and M is a metal ion chelator.

8. The compound of claim 1, wherein the chelator comprises a single thiol-containing group.

9. The compound of claim 8, wherein the single thiol-containing group has a formula:

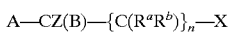

wherein A is H, HOOC—, $H_2$NOC—, —NHOC—, —OOC—, $R^e{}_2$NOC—, or $R^d$; B is H, SH, —NHR$^c$, —N(R$^c$)— or $R^d$; Z is H or $R^d$; X is SH, —NHR$^c$, —N(R$^c$)— or $R^d$; $R^a$, $R^b$, $R^c$ and $R^d$ are independently H, straight chain $C_1$–$C_8$ alkyl, branched chain $C_1$–$C_8$ alkyl, or cyclic $C_3$–$C_8$ alkyl; n is 0, 1 or 2; $R^e$ is $C_1$–$C_4$ alkyl, an amino acid, or a peptide comprising 2 to about 10 amino acids; and: (1) where B is —NHR$^c$ or —N(R$^c$)—, X is SH and n is 1 or 2; (2) where X is —NHR$^c$ or —N(R$^c$)—, B is SH and n is 1 or 2; (3) where B is H or $R^d$, A is HOOC—, $H_2$NOC—, —NHOC—, or —OOC—, X is SH and n is 0 or 1; (4) where A is H or $R^d$, then where B is SH, X is —NHR$^c$ or —N(R$^c$)— and where X is SH, B is —NHR$^c$ or —N(R$^c$)— and n is 1 or 2; (5) where X is H or $R^d$, A is HOOC—, $H_2$NOC—, —NHOC—, or —OOC— and B is SH; (6) where Z is methyl, X is methyl, A is HOOC—, $H_2$NOC—, —NHOC—, or —OOC— and B is SH and n is 0; and (7) where B is SH, X is not SH and where X is SH, B is not SH.

10. A compound having a formula:

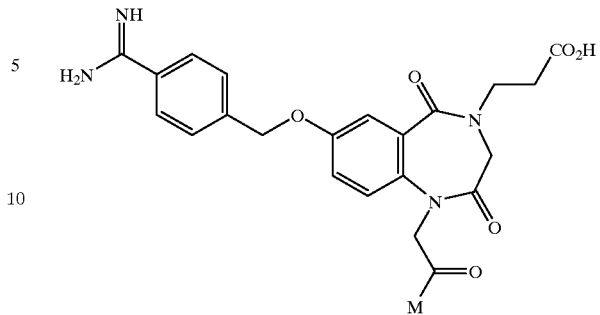

wherein M is a metal ion chelator.

11. The compound of claim 10, wherein M is selected from the group consisting of:

a)

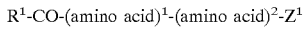

wherein (amino acid)$^1$ and (amino acid)$^2$ are each independently any primary α- or β-amino acid that does not comprise a thiol group, $Z^1$ is selected from the group consisting of cysteine, homocysteine, isocysteine, penicillamine, 2-mercaptoethylamine, 2-mercaptopropylamine, 2-mercapto-2-methylpropylamine, and 3-mercaptopropylamine, and $R^1$ is lower ($C_1$–$C_4$) alkyl, or $R^1$—CO is an amino acid, a peptide, or (aa)-peptide, wherein (aa) is any α- or β-amino acid not comprising a thiol group;

wherein when $Z^1$ is cysteine, homocysteine, isocysteine or penicillamine, $Z^1$ comprises a carbonyl group covalently linked to a hydroxyl group, a $NR^3R^4$ group, wherein each of $R^3$ and $R^4$ are independently H, a bond, lower ($C^1$–$C^4$) alkyl, an amino acid or a peptide comprising from 2 to 10 amino acids; and b)

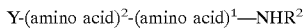

wherein (amino acid)$^1$ and (amino acid)$^2$ are each independently any primary α- or β-amino acid that does not comprise a thiol group Y is selected from the group consisting of cysteine, homocysteine, isocysteine, penicillamine, 2-mercaptoacetate, 2-mercaptopropionate, 2-mercapto-2-methylpropionate, 3-mercaptopropionate, and $R^2$ is H, a bond, lower ($C^1$–$C^4$) alkyl, and $NHR^2$ is an amino acid, a peptide, or (aa)-peptide peptide, wherein (aa) is any α- or β-amino acid not comprising, a thiol group;

wherein when Y is cysteine, homocysteine, isocysteine or penicillamine, Y comprises an amino group covalently linked to —H, an amino acid, a peptide, or (aa)-peptide peptide, wherein (aa) is any α- or β-amino acid not comprising a thiol group.

12. The compound of claim 10, wherein M is selected from the group consisting of:

-Gly-Gly-Cys, -Gly-Gly-Cys.amide, Gly-Gly-Cys-, Cys-Gly-Gly-, -Gly-Gly-Gly-Cys (SEQ ID NO: 1), -Gly-Gly-Gly-Cys.amide (SEQ ID NO:1), Arg-Gly-Cys-, -(ε-Lys)-Gly-Cys-, -(δ-Orn)-Gly-Cys-, -(γ-Dab)-Gly-Cys-, and -(β-Dap)-Lys-Cys-.

13. The compound of claim 10, wherein M is -Gly-Gly-Gly-Cys.amide (SEQ ID NO:1).

14. A pharmaceutical composition comprising 1-[(carboxyglycyl-glycyl-glycyl-cysteinamide)methyl]-4-

(2-carboxyethyl)-7-[(4-amidinophenyl)methyl]-3,4-dihydro-1H-1,4-benzodiazepine-2,5-dione trifluoroacetate, in combination with a pharmaceutically acceptable carrier or diluent.

15. The composition of claim 14, further comprising $^{99m}$Tc.

16. A scintigraphic imaging agent comprising a γ-emitting radionuclide and a compound comprising a glycoprotein IIb/IIIa receptor binding benzodiazepine covalently linked to a metal ion chelating moiety, wherein the compound has an $IC_{50}$ for inhibition of human platelet aggregation of less than about 1 μM, as measured in a standard inhibition of platelet aggregation assay.

17. The agent of claim 16, wherein the radionuclide is $^{99m}$Tc.

18. A complex of a γ-emitting radionuclide and a compound comprising a glycoprotein IIb/IIIa receptor binding benzodiazepine covalently linked to a metal ion chelating moiety, wherein the compound has an $IC_{50}$ for inhibition of human platelet aggregation of less than about 1 μM, as measured in a standard inhibition of platelet aggregation assay.

19. The complex of claim 18, wherein the radionuclide is $^{99m}$Tc.

20. A $^{99m}$Tc chelate of a compound comprising a glycoprotein IIb/IIIa receptor binding benzodiazepine covalently linked to a metal ion chelating moiety, wherein:

a) the compound has an $IC_{50}$ for inhibition of human platelet aggregation of less than about 1 μM, as measured in a standard inhibition of platelet aggregation assay; and b) the chelate contains at least one sulfur ligand bound to $^{99m}$Tc.

21. A method of detecting a thrombus in a mammalian body, comprising the steps of administering an effective diagnostic amount of the composition of claim 15 to the body and detecting radiation localized at the thrombus.

22. A method of detecting a thrombus in a mammalian body, comprising the steps of administering an effective diagnostic amount of the agent of claim 17 to the body and detecting radiation localized at the thrombus.

23. A method of detecting a thrombus in a mammalian body, comprising the steps of administering an effective diagnostic amount of the complex of claim 19 to the body and detecting radiation localized at the thrombus.

24. A method of detecting a thrombus in a mammalian body, comprising the steps of administering an effective diagnostic amount of the chelate of claim 20 to the body and detecting radiation localized at the thrombus.

25. A kit comprising a sealed vial containing:

a) a predetermined quantity of 1-[(carboxyglycyl-glycyl-glycyl-cysteinamide)methyl]-4-(2-carboxyethyl)-7-[(4-amidinophenyl)methyl]-3,4-dihydro-1H-1,4-benzodiazepine-2,5-dione trifluoroacetate; and b) a reducing agent.

* * * * *

```
                          SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 1

Gly Gly Gly Cys
```